United States Patent
Fitzmaurice et al.

(10) Patent No.: US 6,190,358 B1
(45) Date of Patent: *Feb. 20, 2001

(54) REINFORCED RAPID EXCHANGE BALLOON CATHETER

(75) Inventors: Thomas K. Fitzmaurice; Paul Gilson, both of Galway (IE)

(73) Assignee: Medtronic AVE, Inc., Santa Rosa, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/859,654

(22) Filed: May 20, 1997

Related U.S. Application Data

(63) Continuation of application No. 08/737,055, filed as application No. PCT/US95/02783 on Feb. 24, 1995, now abandoned.

(51) Int. Cl.⁷ .................................................. A61M 31/00
(52) U.S. Cl. .............................. 604/103.04; 604/102.02; 604/103.09; 604/96.01; 604/524; 606/192
(58) Field of Search ............................. 604/96, 103, 280, 604/282, 523, 524, 526, 96.01, 102.02, 103.04, 103.09; 606/191, 194, 192

(56) References Cited

U.S. PATENT DOCUMENTS

| | | | |
|---|---|---|---|
| 4,142,531 | | 3/1979 | MacGovern et al. . |
| 4,917,104 | | 4/1990 | Rebell . |
| 5,061,273 | * | 10/1991 | Yock ..................................... 606/194 |
| 5,156,594 | * | 10/1992 | Keith ..................................... 604/96 |
| 5,246,014 | | 9/1993 | Williams et al. . |
| 5,279,562 | * | 1/1994 | Sirhan et al. ........................... 604/96 |
| 5,282,845 | | 2/1994 | Bush et al. . |
| 5,300,025 | * | 4/1994 | Wantink .................................. 604/96 |
| 5,328,472 | * | 7/1994 | Steinke et al. ........................ 604/102 |
| 5,344,402 | | 9/1994 | Crocker . |
| 5,387,193 | * | 2/1995 | Miraki .................................... 604/96 |
| 5,387,226 | * | 2/1995 | Miraki .................................. 606/194 |
| 5,389,087 | * | 2/1995 | Miraki .................................. 604/247 |
| 5,413,559 | * | 5/1995 | Sirhan et al. ......................... 604/102 |
| 5,425,711 | * | 6/1995 | Ressemann et al. .................... 604/96 |
| 5,458,613 | * | 10/1995 | Gharibadeh et al. ................. 606/194 |
| 5,470,315 | * | 11/1995 | Adams ................................... 604/96 |
| 5,516,336 | * | 5/1996 | McInnes et al. ...................... 606/194 |
| 5,531,689 | * | 7/1996 | Burns et al. ........................... 604/99 |
| 5,533,968 | * | 7/1996 | Muni et al. ............................ 604/96 |
| 5,545,133 | * | 8/1996 | Buras et al. ........................... 604/96 |
| 5,545,134 | * | 8/1996 | Hilaire et al. .......................... 604/96 |
| 5,549,556 | * | 8/1996 | Ndondo-Lay et al. ............... 604/102 |
| 5,556,382 | * | 9/1996 | Adams ................................... 604/96 |
| 5,626,600 | * | 5/1997 | Harzewski et al. .................. 606/194 |
| 5,634,902 | * | 6/1997 | Johnston et al. ....................... 604/96 |
| 5,695,468 | * | 12/1997 | Lafontaine et al. .................... 604/96 |
| 5,743,874 | * | 4/1998 | Fischell et al. ......................... 604/96 |
| 5,743,875 | * | 4/1998 | Sirhan et al. ........................... 604/96 |
| 5,823,995 | * | 10/1998 | Fitzmaurice et al. .................. 604/96 |
| 6,030,405 | * | 2/2000 | Zarbatany et al. ................... 606/191 |

* cited by examiner

*Primary Examiner*—John G. Weiss
*Assistant Examiner*—Cris L. Rodriguez

(57) ABSTRACT

The invention is a dilation catheter which comprises an elongated catheter shaft, a guide wire tube, and an angioplasty balloon. The distal end of the balloon is attached to the distal portion of the guide wire tube, and the proximal portion of the balloon is attached to the distal portion of the catheter shaft. A stiffening wire is attached to the inner wall of the catheter shaft at a plurality of points along its length. The distal extremity of the guide wire tube is decreased in size relative to the proximal portion of the guide wire tube. A fluid is contained within the guide wire lumen.

11 Claims, 3 Drawing Sheets

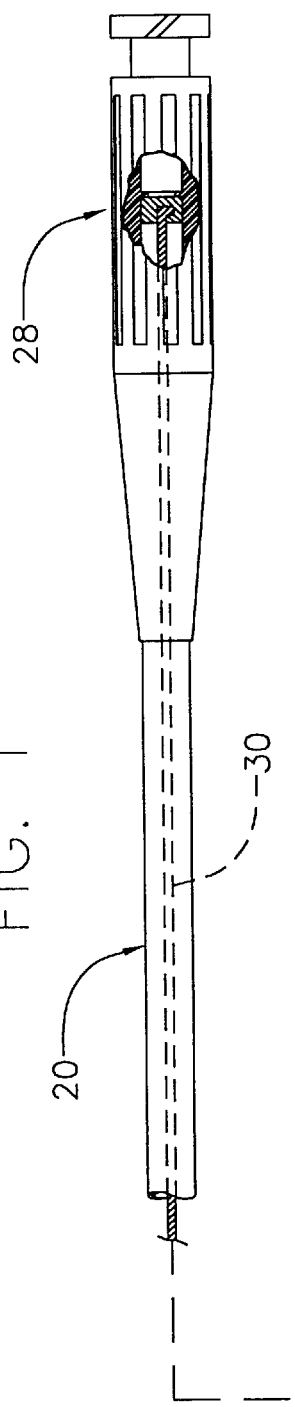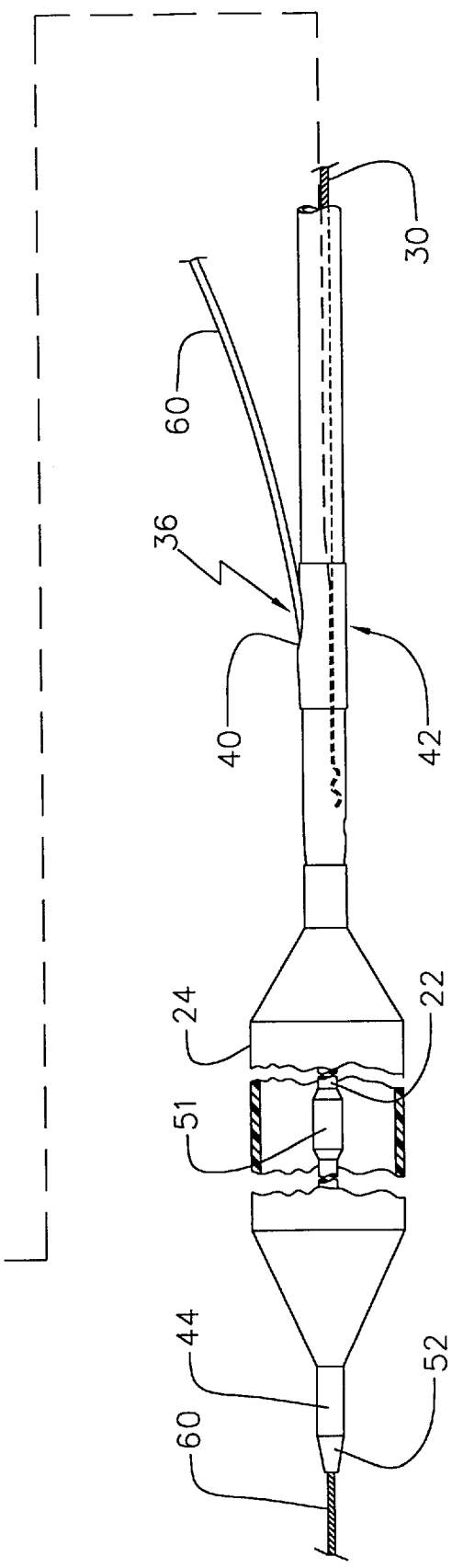

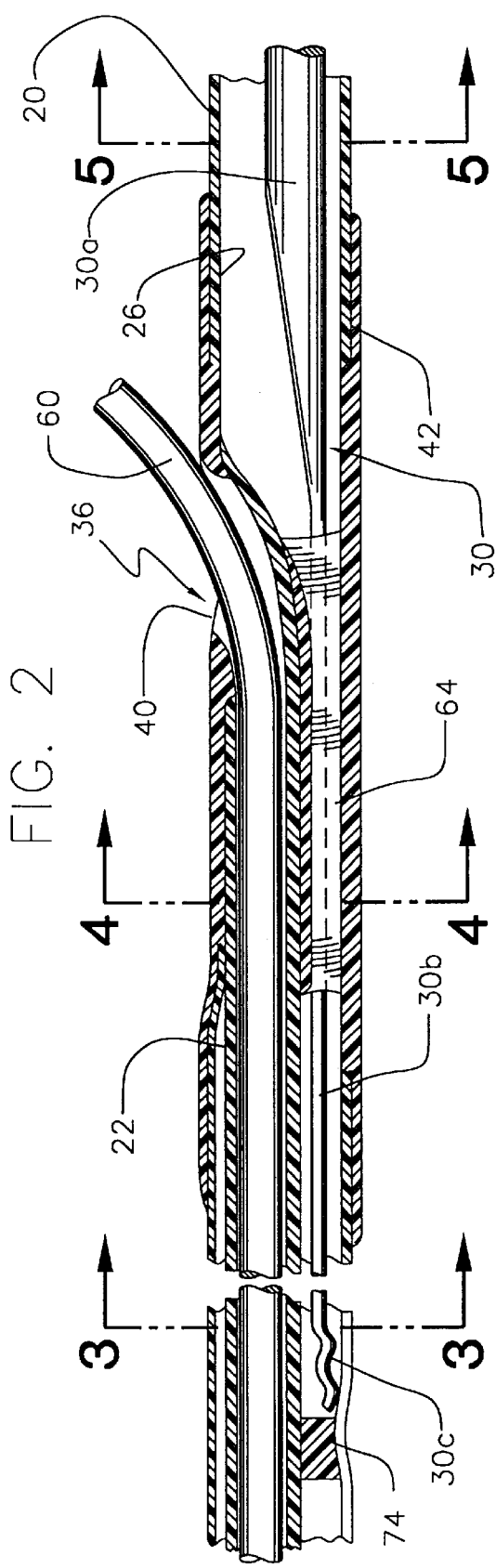

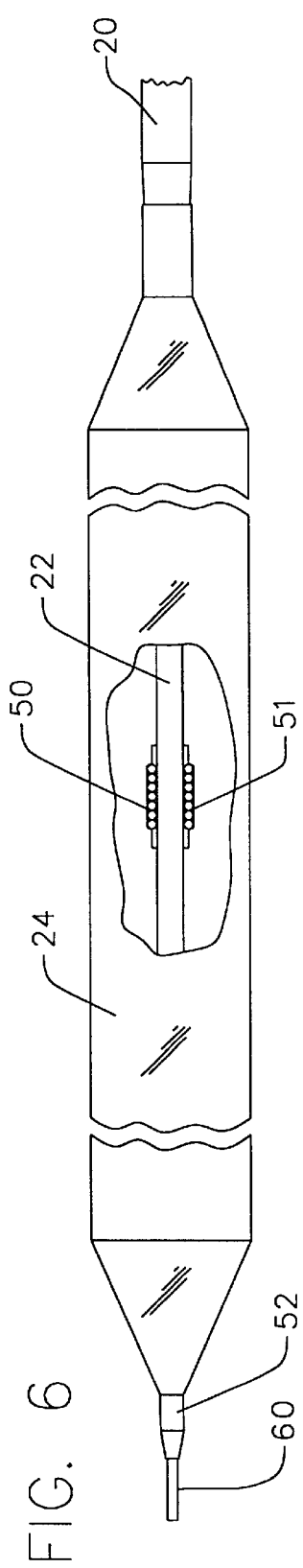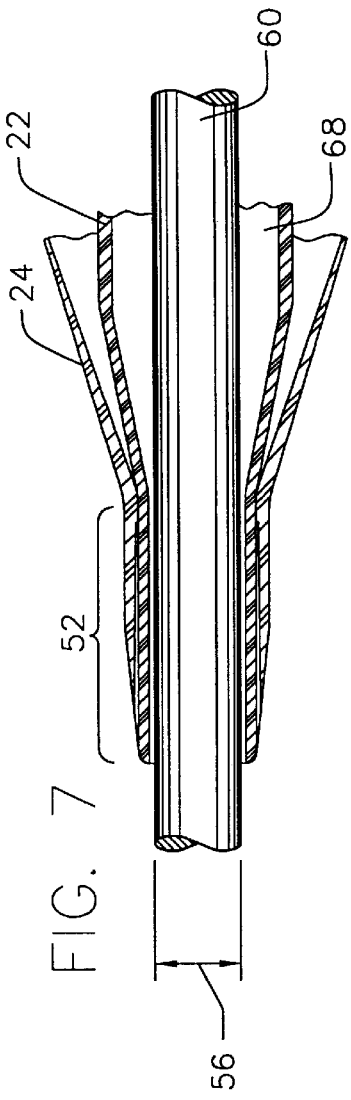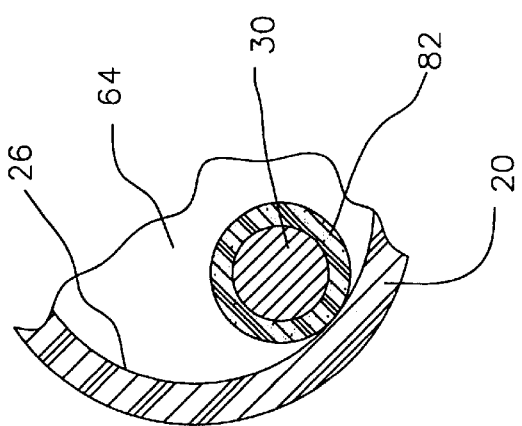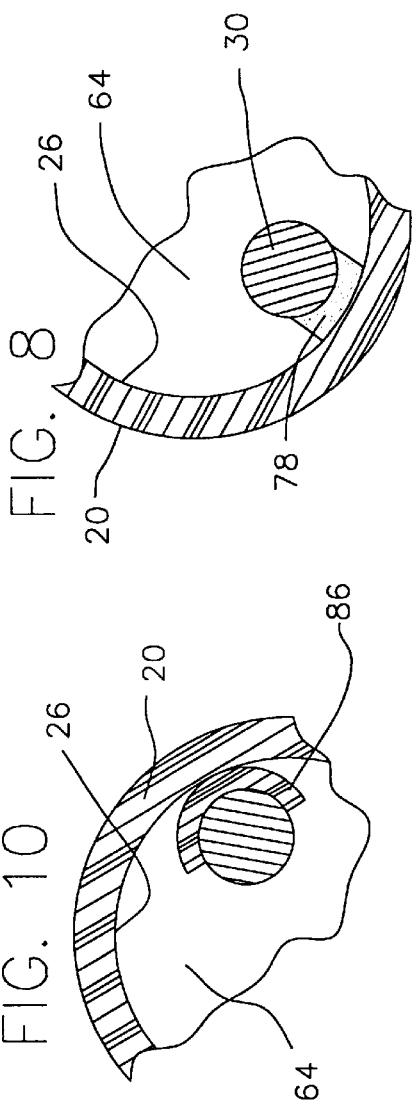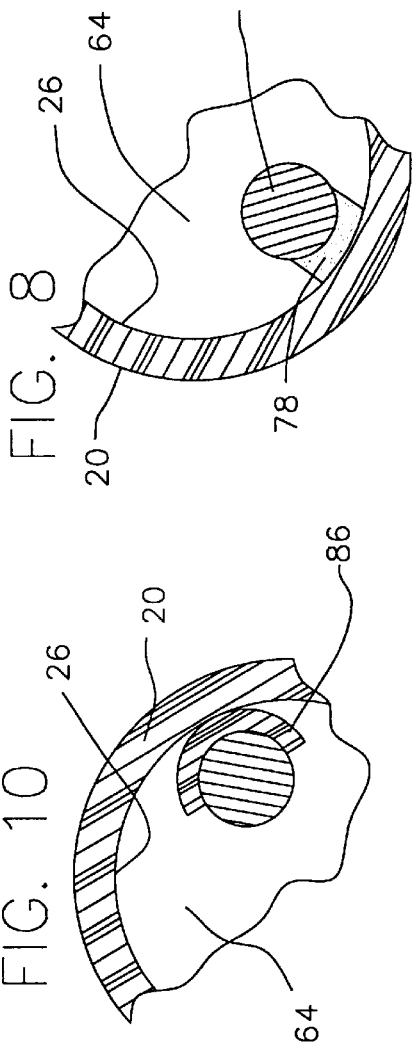

REINFORCED RAPID EXCHANGE BALLOON CATHETER

The present Application is a Continuation Application of U.S. patent application Ser. No. 08/737,055 filed on Oct. 24, 1996, (abandoned), which is the U.S. National Phase Application of PCT/US95/02783, filed on Feb. 24, 1995, (published as WO 96/25970 on Aug. 20, 1996).

FIELD OF THE INVENTION

This invention relates to a dilatation catheter and more particularly to a dilatation catheter construction of particular utility as a rapid exchange dilatation catheter.

BACKGROUND OF THE INVENTION

Rapid exchange dilatation catheters are becoming increasingly popular in angioplasty procedures because, unlike over-the-wire catheters that require guide wire extenders to perform a catheter exchange, the rapid exchange dilatation catheter construction enables one rapid exchange dilatation catheter to be exchanged readily for another. U.S. Pat. No. 4,762,129 to Bonzel discloses one such catheter having a guide wire lumen only at the distal segment of the catheter, for coupling the catheter and the guide wire together. The guide wire tube extends through the balloon, from the distal end of the catheter to a point proximal to the balloon. Rapid exchange and manipulation of the dilatation catheter is facilitated because the catheter segment in contact with the surface of the guide wire is only as long as the balloon.

Although conventional rapid exchange-type catheters allow rapid catheter exchange, they tend to lack stiffness along their shaft length proximal to the exchange joint, at which point, the catheter gains the benefit of the guide wire to impart stiffness to the catheter. This lack of stiffness along the proximal portion of the catheter makes it difficult to advance the catheter through the body passageway. Bonzel addresses this problem, in part, by providing an integral stabilizing means that extends from the catheter's proximal end, through the inflation lumen, to the distal end of the balloon.

The use of a stiffening wire (or mandrel) has also been proposed in a rapid exchange catheter to provide controlled stiffness where needed without diminishing flexibility in the distal section of the catheter. Such stiffening wires, however, can buckle under compressive loads and present a potential risk of perforating the catheter wall.

The invention provides an improved rapid exchange dilatation catheter which incorporates a stiffening wire wherein the likelihood of buckling and/or perforation of the catheter shaft is substantially reduced if not eliminated.

Another feature of the invention is applicable to all balloon catheters containing guide wire lumens, for example, both over-the-wire and rapid exchange catheters. In such catheters, the guide wire lumen is normally flushed prior to use with a saline/heparin mixture to prevent blood coagulation in the lumen. The guide wire lumen must be large enough to permit free movement of the catheter relative to the guide wire. The larger the gap between the guide wire lumen and the guide wire, the freer the movement, but a smaller gap reduces the catheter profile in the distal region of the catheter, thus facilitating introducing the catheter across the stenosis.

U.S. Pat. No. 5,209,728 to Kraus et al. addresses the problem of having blood enter the catheter, and discloses a catheter provided with a tip member adapted to slidably receive a specially formed guide wire, so as to ensure a liquid-tight seal between the catheter and guide wire. The liquid-tight seal is formed by bringing the inner surface of the catheter sufficiently close to the outer surface of the guide wire. Consequently, the inflation fluid is retained within the catheter, and blood is kept out of the catheter.

However, as is typically the case with over-the-wire catheters, a reduced space between the catheter and the guide wire restricts the clear movement of the guide wire relative to the catheter. Such resistance increases the tendency of the catheter to buckle when the operator attempts to advance the catheter through the body passageway. It would, therefore, be desirable to provide a flexible dilatation catheter having a stiffening wire adapted to impart stiffness to the catheter to prevent buckling as it is manipulated through the body passageway. It would also be desirable to provide such a catheter that limits the amount of blood that enters the catheter, while at the same time, facilitates the free movement of the guide wire with respect to the catheter.

The invention further provides a balloon catheter which is movable with respect to a guide wire, wherein the profile of the distal region of the catheter is reduced without a sacrifice in freedom of movement of the catheter relative to the guide wire.

SUMMARY OF THE INVENTION

The present invention is directed towards a dilatation catheter which comprises an elongated catheter shaft, a guide wire tube and an angioplasty balloon. In conventional fashion, the distal end of the balloon is attached to the distal portion of the guide wire tube and the proximal portion of the balloon is attached to the distal portion of the catheter shaft. The first aspect of the invention is directed towards positioning a stiffening wire having a large diameter proximal portion and a small diameter distal portion, within the catheter shaft. The stiffening wire is attached to the inner wall of the catheter shaft at a plurality of points along its length, thereby providing strength to the proximal portion of the catheter, without compromising the size of the inflation/deflation lumen.

The second feature of the invention is applicable to any catheter that includes a guide wire lumen, such as an over-the-wire catheter or a rapid exchange or rapid exchange catheter. According to this feature of the invention, a guide wire lumen is provided with a relatively large gap between the guide wire and the inner surface of the guide wire tube. The distal extremity of the guide wire tube is decreased in size for a short distance. The diameter of this decreased distal extremity approximates the diameter of the guide wire, thereby, substantially reducing the amount of blood that can enter the guide wire lumen. The large diameter portion of the guide wire lumen contains a saline/heparin mix which, because it is less viscous than blood, tends to flow into the gap within the small diameter lumen portion to reduce blood coagulation in that portion and thereby reduce the risk of "seizing." The relative movement between the balloon catheter and the wire creates a wiping action which keeps the wire clean.

The outer diameter of the distal extremity of the guide wire tube is also reduced or tapered. As a result of this taper, the catheter profile in the distal region of the catheter is reduced, facilitating passage of the catheter across a stenosis. As a result of the tapered guide wire tube, the profile of the distal portion of the balloon is appreciably decreased when the balloon is in its collapsed state. This further facilitates positioning the balloon across a stenosis.

BRIEF DESCRIPTION OF THE DRAWINGS

The foregoing and other features of the present invention will be more readily apparent from the following detailed description and drawings of a preferred embodiment of the invention in which:

FIG. 1 is a schematic plan view of a dilatation catheter in accordance with the invention;

FIG. 2 is a detailed cross-sectional view of a catheter according to a preferred embodiment of the invention, illustrating the exchange joint in detail;

FIG. 3 is a cross-sectional view along line 3—3 of FIG. 2;

FIG. 4 is a cross-sectional view along line 4—4 of FIG. 2, showing the fused laminate in the exchange joint region;

FIG. 5 is a cross-sectional view along line 5—5 of FIG. 2;

FIG. 6 shows the balloon section of the catheter, illustrating the radiopaque coil spring;

FIG. 7 illustrates the tapered distal end of the catheter, showing the reservoir formed inside the guide wire lumen;

FIG. 8 illustrates, in cross-section, a preferred method of attaching the stiffening wire to the inner wall of the catheter shaft;

FIG. 9 illustrates, in cross-section, a second method for attaching the stiffening wire to the inner wall of the catheter shaft; and FIG. 10 illustrates, in cross-section, another method for attaching the stiffening wire to the inner wall of the catheter shaft.

DETAILED DESCRIPTION OF A PREFERRED EMBODIMENT OF THE INVENTION

A preferred embodiment of the invention as illustrated in FIGS. 1 and 2 is a rapid exchange or monorail dilatation catheter comprising an elongated catheter shaft 20, a guide wire tube 22 (FIG. 2) and an angioplasty balloon 24.

In conventional fashion, the distal end of balloon 24 is attached to the distal portion of the guide wire tube 22 and the proximal portion of the balloon is attached to the distal portion of the catheter'shaft 20. The balloon 24 is formed from suitable balloon material, for example, polyethylene terephthalate ("PET"), nylon, or urethane. It is preferred that the balloon 24 be coated with a highly lubricous, abrasion resistant coating. An example of this preferred coating is that disclosed in U.S. Pat. No. 5,077,352 to Elton, and assigned to the assignee of the present invention, C. R. Bard, of Murray Hill, N.J. The Elton '352 patent is incorporated by reference as if set forth in its entirety herein.

As shown if FIG. 7, the wall thickness of the balloon 24 is not uniform. Considering only the distal sloping portion of the balloon 24, the wall of the balloon 24 is constructed such that the wall is very thin at the top of the sloping portion of the balloon, and becomes increasingly thicker as one proceeds distally, down the sloping portion of the balloon to where the balloon 24 comes in contact with the guide wire tube 22. In a conventional catheter construction having a balloon attached to the catheter shaft, this thick-walled section of the balloon contributes significantly to the increased balloon profile at the leading edge of the balloon.

According to the invention, however, the balloon 24 profile is reduced (1) by attaching the distal portion of the balloon 24 directly to the guide wire tube 22, typically of a smaller outer diameter than the catheter shaft 20, and (2) by tapering the guide wire tube 22 in the distal region. When the balloon 24 is in its collapsed state, the thickest segment of the wall of the balloon 24 corresponds to the tapered outer diameter segment of the guide wire tube 22, thus reducing the balloon.-profile in the relevant distal portion of the balloon 24.

As shown in FIG. 6, a radiopaque coil spring 50 is positioned within the balloon 24 around the guide wire tube 22. A thin walled protective sleeve 51 is placed over the coil spring. The radiopaque coil spring 50 enables the balloon 24 to be identified under X-ray fluoroscopy. The coil may be formed from, for example, 0.0025 inch spring coil material such as a gold-platinum combination, and is approximately 4.5 millimeters long. The chosen coil parameters depend on the desired flexibility characteristics to be imparted to the distal end of the catheter.

The balloon 24 is in fluid communication with the proximal end of the catheter via the annular space 64 between the catheter shaft 20 and the stiffening wire 30a which forms an inflation/deflation lumen (FIG. 5). The inflation/deflation lumen 65 is maintained through the exchange joint region 36 as explained below in the discussion of the exchange joint region 36 (FIG. 4). Distal of the exchange joint region 36, the inflation/deflation lumen occupies the annular space between the guide wire tube 22, the catheter shaft 20, and the distal reduced diameter portion 30b of the stiffening wire 30 (FIG. 3). Fluid, introduced through a connector at the luer fitting 28, causes the balloon 24 to expand in conventional fashion.

The catheter shaft 20 extends distally from the luer fitting 28 and terminates at the proximal end of the balloon 24 (FIG. 1). The catheter shaft 20 is skived at the point where a guide wire 60 is introduced, forming a guide wire port 40. The portion of the catheter shaft 20 around the guide wire port 40, namely, the exchange joint region 36, is subjected to increased stresses because the skive compromises the integrity of the catheter shaft 20. For additional strength, an exchange joint sleeve 42 may be fused to the catheter shaft 20 in the exchange joint region 36. The exchange joint sleeve 42 is preferably made from the same material as the catheter shaft 20, for example, polyethylene.

To further stiffen the catheter in the region of the exchange joint 36, the guide wire tube 22 may be fused together with the catheter shaft 20 and the exchange joint sleeve 42, to form a fused polyethylene laminate 46 (illustrated in cross-section in FIG. 4). In a preferred construction employing the fused laminate option, a flat mandrel (not shown) is temporarily positioned between the guide wire tube 22 and the catheter shaft 20 to ensure that a fluid passageway (inflation/deflation lumen) is maintained through the fused laminate structure 46 after heat welding. A patency mandrel (not shown) is also placed inside the guide wire tube 22. A removable shrink tubing is placed over the exchange joint region 36 and a heat source is applied to the portion of the exchange joint region 36 where the fused laminate 46 is desired. After the fused laminate 46 is formed, the shrink tubing is removed, and the patency mandrel and the flat mandrel are withdrawn. As shown in FIG. 4, the distal reduced diameter portion 30b of the stiffening wire 30 is embedded within the fused laminate 46.

In the preferred embodiment of the invention, the stiffening wire 30, positioned within the catheter shaft 20, extends longitudinally from the luer fitting 28 to a point proximal to the balloon 24. As shown in the proximal cut-away section of FIG. 1, the proximal end of the stiffening wire is bent to form a right-angled hook or flag. Plastic is molded over this hook to form a button which snaps into a corresponding detent within the luer fitting.

The precise point at which the stiffening wire 30 terminates is not critical to the invention, and will depend on the desired flexibility in the distal portion of the catheter.

According to the invention, the stiffening wire 30 is attached at spaced locations along its length to the inner wall 26 of the catheter shaft 20. The stiffening wire 30 is preferably attached by a plurality of wire "tacks" 78 (FIG. 8). These wire tacks 78 are conveniently made from polyethylene, and are attached to the stiffening wire 30 before the stiffening wire 30 is inserted into the catheter. After the stiffening wire 30 has been placed within the catheter shaft 20, the wire tacks 78 are welded, glued, thermally adhered, or otherwise attached to the inner wall 26 of the catheter shaft 20. In a preferred construction, 3 two millimeter long wire tacks 78 are spaced apart along the stiffening wire 30. The first wire tack 78 is located approximately 40 centimeters proximal of the exchange joint 36. The second and third wire tacks 78 are located approximately 63 and 86 centimeters proximal of the exchange joint 36 respectively.

Numerous methods may be employed to periodically attach the stiffening wire 30 to the inner wall of the catheter shaft 20. For example, in another embodiment of the invention, sleeves 82 are used in place of the wire tacks 78. The sleeves 82, wrapped around the stiffening wire 30, are adhered to the inner wall 26 of the catheter shaft 20 (FIG. 9). In yet another example, the stiffening wire 30 may be adhesively bonded to extruded material 86 and welded to the inner wall 26 of the catheter shaft 20 (FIG. 10). Preferably, the wire tacks 78, the sleeves 82, and the extruded material 86 are made from the same material as the catheter shaft 20, for example, polyethylene.

By locking the stiffening wire 30 to the inner wall 26 of the catheter shaft 20, the likelihood of the shaft buckling is reduced, and the compressive force that can be applied to the proximal end of the catheter is increased. Also, by using very small wire tacks 78 to attach the stiffening wire 30 at periodic points along its length, the largest possible inflation lumen 64 is maintained through the catheter shaft 20, thereby, decreasing inflation and deflation times.

As shown in FIG. 2, the stiffening wire 30 has a large diameter proximal portion 30a and a smaller diameter or tapered distal portion 30b in the region of the exchange joint 36. The smaller diameter portion 30b of the stiffening wire 30 imparts increased flexibility to the distal segment of the catheter.

In a preferred embodiment, the stiffening wire 30 has a wave shaped distal end 30c, so that the distal tip of the stiffening wire 30 is deflected upwards, away from the wall of the catheter shaft 20. Even though the stiffening wire 30 is attached along its length, the stiffening wire 30 is capable of some longitudinally movement within the catheter shaft 20. It is, therefore, conceivable that the distal tip would be able to pierce the wall of the catheter shaft 20 as the catheter is manipulated around a tight radius curve. The wave-like distal end 30c keeps the distal tip away from the wall of the catheter shaft 20.

The stiffening wire 30 is preferably made of MP35N alloy. The MP35N alloy is an alloy of nickel, cobalt, molybdenum, and chromium. The MP35N alloy is commercially available from Fort Wayne Metals of Fort Wayne, Ind.

When compared with stainless steel, the MP35N alloy has a higher yield strength, and imparts increased stiffness to the catheter shaft 20 for a given diameter. Therefore, using MP35N alloy reduces the probability that the catheter shaft 20 will buckle as the catheter is advanced around a tight radius.

In a rapid exchange catheter as shown, the guide wire tube 22 extends for only the distal portion of the catheter (for example, about twenty-five cm). The proximal end of the guide wire tube 22 forms the exchange joint 36 where the guide wire 60 can be introduced into the guide wire tube 22 (FIG. 2). The guide wire tube 22 is preferably made of the same material as the catheter shaft 20, for example, a flexible heat shrinkable material such as high density polyethylene.

As shown in FIG. 7, the guide wire tube 22 extends distally from the exchange joint 36 to the distal end of the catheter 20. According to the present invention, the distal extremity 52 of the guide wire tube 22 is decreased in size for a short distance. The inside diameter of the distal extremity 52 approximates the diameter of the guide wire 60, thereby, substantially reducing the amount of blood that can enter the guide wire lumen. The reduced diameter distal extremity 52 is formed by first placing a mandrel within the guide wire tube 22, and then, pulling the guide wire tube 22 through a heated die in order to reduce the diameter of the distal extremity 52 of the guide wire tube 22 to approximate the size of the mandrel. The mandrel is then removed.

Although a rapid exchange catheter is illustrated in FIG. 7, this aspect of the invention is equally applicable to over-the-wire dilatation catheters and any other catheter containing a guide wire tube.

An anticoagulant is injected into the guide wire lumen 68 as the catheter is being prepared, before the catheter is inserted into the patient. The anticoagulant remains primarily in the large diameter portion of the guide wire lumen 68 (exaggerated in FIG. 7 for added clarity). In a preferred rapid exchange catheter construction, the proximal end of the guide wire tube is not sealed and a small quantity of the anticoagulant will escape from the proximal end. However, the adhesion of the anticoagulant to the inner surface of the guide wire tube 22 is sufficient to maintain a satisfactory amount of anticoagulant within the guide wire lumen.

Because the anticoagulant is less viscous than blood, it tends to occupy the gap within the small diameter lumen portion. As the guide wire 60 is moved relative to the catheter, the presence of the anticoagulant "wipes" the guide wire 60 clean. This wiping action prevents any blood that may enter the guide wire lumen 68 from clotting along the guide wire 60. The anticoagulant is preferably a saline/heparin mixture when the catheter is used in a blood vessel or artery, for example, a coronary artery.

A cross-link joint 74 is illustrated in FIG. 2 and may be employed to connect the catheter shaft 20 to the guide wire tube 22, preferably in the region between the balloon 24 and the exchange joint 36 (FIG. 2). The cross-link joint 74 efficiently couples the compressive force from the catheter shaft 20 to the distal tip 52 of the catheter. As the operator pushes on the catheter shaft 20, the cross-link joint 74 transmits this force to the guide wire tube 22, thereby preventing any deformation at the distal portion of the catheter.

The cross-link joint 74 may comprise an additional "block" of polyethylene that is fused, spot welded, or otherwise attached to both the inner wall of the catheter shaft 20 and to the guide wire tube 22. The cross-link joint 74 may, for example, be positioned at a location approximately 5 millimeters from the distal tip of the stiffening wire 30, and approximately 6 centimeters from the proximal end of the balloon 24.

All dimensions given in this detailed description are for illustrative purposes only, and unless otherwise indicated, are not critical to the present invention.

While the invention has been particularly shown and described with reference to a preferred embodiment thereof, it will be understood by those skilled in the art that various changes in form and details may be made therein without departing from the spirit and scope of the invention.

What is claimed is:

1. A dilatation catheter, comprising:

an elongated catheter shaft having an outer wall and inner wall, the inner wall surrounding a central lumen, a guide wire tube having a distal portion of a first length, a proximal portion of a second length longer than the first length, an outer surface and an inner surface, wherein the guide wire tube extends through at least a distal portion of the catheter shaft, with a fluid channel between the outer surface of the guide wire tube and the inner wall of the catheter shaft, wherein the inner surface of the guide wire tube forms a lumen for receiving a guide wire the lumen having a first diameter for the distal portion of the guide wire tube and a second diameter larger than the first diameter for the proximal portion of the guide wire tube, a balloon having a distal end and a proximal end, the proximal end being attached to the distal portion of the catheter shaft, and the distal end being attached to the distal portion of the guide wire tube, the fluid channel serving as an inflation/deflation lumen for the balloon, wherein the first length of the distal portion of the guide wire tube and the first diameter for the distal portion of the guide wire tube being selected such that when a guide wire is within the guide wire lumen, blood is substantially prevented from entering the proximal portion of the guide wire lumen and a less viscous anticoagulant in the proximal portion of the guide wire lumen is allowed to coat the surface of the guide wire within the distal portion of the guide wire lumen.

2. The dilatation catheter as in claim 1 wherein the outer diameter of the distal portion of the guide wire tube is smaller than the outer diameter of the proximal portion of the guide wire tube.

3. The dilatation catheter as in claim 1 wherein the proximal portion of the guide wire lumen is adapted to receive an anticoagulant solution.

4. The dilatation catheter as in claim 3 wherein the anticoagulant solution is a heparin/saline mixture.

5. The dilatation catheter as in claim 1 further comprising a stiffening wire positioned within the catheter shaft.

6. The dilatation catheter as in claim 5 wherein the stiffening wire is attached to the inner wall of the catheter shaft at at least two spaced locations.

7. The dilatation catheter as in claim 6 wherein a plurality of wire tacks are used to attach the stiffening wire to the inner wall of the catheter shaft at the spaced locations.

8. The dilatation catheter as in claim 6 wherein a plurality of sleeves are used to attach the stiffening wire to the inner wall of the catheter shaft at the spaced locations.

9. The dilatation catheter as in claim 5 wherein the stiffening wire is made of MP35N alloy.

10. A rapid exchange dilation catheter, comprising:

an elongated catheter shaft having a proximal portion, a distal portion, an outer surface, an inner surface and an exchange joint, the inner surface surrounding a central lumen, a guide wire tube having a proximal portion, a distal portion, an outer surface and an inner surface, the inner surface surrounding a guide wire lumen for receiving a guide wire, the guide wire tube extending from the exchange joint in the catheter shaft through the distal portion of the catheter shaft, with a fluid channel between the outer surface of the guide wire tube and the inner surface of the catheter shaft;

a balloon having a proximal end and a distal end, wherein the balloon is connected at its distal end to the distal portion of the guide wire tube and at its proximal end to the distal portion of the catheter shaft, wherein the fluid channel serves as an inflation/deflation lumen for the balloon; and a stiffening wire positioned within the proximal portion of the catheter shaft and attached thereto at at least two spaced apart locations, the stiffening wire including wire tacks associated therewith at the spaced apart locations, the wire tacks being thermally bonded to the proximal shaft.

11. A rapid exchange dilation catheter, comprising:

an elongated catheter shaft having a proximal portion, a distal portion, an outer surface, an inner surface and an exchange joint, the inner surface surrounding a central lumen, a guide wire tube having a proximal portion, a distal portion, an outer surface and an inner surface, the inner surface surrounding a guide wire lumen for receiving a guide wire, the guide wire tube extending from the exchange joint in the catheter shaft through the distal portion of the catheter shaft, with a fluid channel between the outer surface of the guide wire tube and the inner surface of the catheter shaft;

a balloon having a proximal end and a distal end, wherein the balloon is connected at its distal end to the distal portion of the guide wire tube and at its proximal end to the distal portion of the catheter shaft, wherein the fluid channel serves as an inflation/deflation lumen for the balloon; and a stiffening wire positioned within the proximal portion of the catheter shaft and attached thereto at at least two spaced apart locations, the stiffening wire including sleeves associated therewith at the spaced apart locations, the sleeves being thermally bonded to the proximal shaft.

* * * * *

UNITED STATES PATENT AND TRADEMARK OFFICE
CERTIFICATE OF CORRECTION

PATENT NO. : 6,190,358 B1 Page 1 of 1
DATED : February 20, 2001
INVENTOR(S) : Fitzmaurice et al.

It is certified that error appears in the above-identified patent and that said Letters Patent is hereby corrected as shown below:

<u>Title page,</u>
Item [75], Inventors, please add -- Patrick J.E. Duane (Galway, IE) --

Signed and Sealed this

Eleventh Day of November, 2003

JAMES E. ROGAN
*Director of the United States Patent and Trademark Office*